United States Patent [19]
Khairkhahan

[11] Patent Number: 5,607,404
[45] Date of Patent: Mar. 4, 1997

[54] LOW FRICTION INNER LUMEN

[75] Inventor: Kourosh Khairkhahan, Palo Alto, Calif.

[73] Assignee: Medtronic, Inc., Minneapolis, Minn.

[21] Appl. No.: 226,205

[22] Filed: Apr. 11, 1994

[51] Int. Cl.[6] ............................................. A61M 25/00
[52] U.S. Cl. ............................... 604/264; 604/280
[58] Field of Search ........................... 604/96, 101, 264, 604/280–282; 128/658

[56] References Cited

U.S. PATENT DOCUMENTS

| | | |
|---|---|---|
| 3,995,623 | 12/1976 | Blake et al. |
| 4,328,806 | 5/1982 | Cooper . |
| 4,406,656 | 9/1983 | Hattler et al. ........................ 604/280 |
| 4,632,108 | 12/1986 | Geil . |
| 4,753,640 | 6/1988 | Nichols et al. ........................ 604/247 |
| 4,947,852 | 8/1990 | Nassi et al. ........................ 128/662.06 |
| 5,163,906 | 11/1992 | Ahmadi ........................ 604/101 |
| 5,271,410 | 12/1993 | Wolzinger et al. ........................ 128/692 |

*Primary Examiner*—John D. Yasko
*Attorney, Agent, or Firm*—Dianne M. Plunkett; Harold R. Patton

[57] ABSTRACT

A catheter body with a single, centrally located guidewire lumen having an odd number of longitudinally extending, generally planar, inner wall surfaces. Each wall surface has a radius of curvature in excess of the guidewire's radius of curvature, as measured in cross section. The wall surfaces are joined to one another by longitudinally extending corner surfaces, each corner surface having a radius of curvature less than the guidewire's radius of curvature, as measured in cross section. The wall surfaces and corner surfaces are formed of alternating thicknesses to the outer diameter.

19 Claims, 2 Drawing Sheets

LOW FRICTION INNER LUMEN

FIELD OF THE INVENTION

The present invention relates to catheters, and more particularly, to noncircular catheter guidewire lumens.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque. If, during the procedure, a catheter must be exchanged for one of a different size, an over-the-wire system is advantageous because the guidewire can be left in place. In over-the-wire systems, the guidewire is threaded through the vascular system to the site of the stenosis and the catheter subsequently tracked over it to the stenosis. The catheter is withdrawn over the guidewire and another catheter can be slid into place over it. If both the catheter and the lumen have a round shape, with substantially equal diameters, tracking can be diminished due to friction between the catheter and the guidewire. In areas where the catheter body is flexed, the lumen wall will deform and contact a substantial percentage of the circumference of the guidewire. Various alternative designs have been proposed to form noncircular lumens. Lumen tubing having noncircular lumens is known in the art as follows.

U.S. Pat. No. 3,995,623, to Blake et al, for "Multipurpose Flow-Directed Catheter", discloses in FIG. 5 a balloon flotation electrode catheter with four noncentrally located, noncircular lumens. The lumens are pie shaped with each having two generally planar, longitudinally extending wall surfaces joined at about a 90 degree angle with those two walls joined by a third curved wall as measured in cross-section. The outer wall thickness is substantially constant.

U.S. Pat. No. 4,328,806, to Cooper, for "Catheter with Trans-Luminal Gas Pathway", discloses in FIGS. 4–6 and FIGS. 9–10, a catheter having at least two separate noncentrally located, noncircular lumens of a pie shape. One lumen is for conveying liquids to and from a port spaced substantially from the distal end of the catheter and the other for enclosing an electrical conductor. The lumens are pie shaped with each having two generally planar, longitudinally extending wall surfaces joined at more than a 90 degree angle with those two walls joined by a third curved wall as measured in cross-section. The outer wall thickness is substantially constant.

U.S Pat. No. 4,632,108, to Geil, for "Tube and Material for Use in Laser Surgery", discloses in FIG. 2, a laser-resistant surgical tube for use in connection with laser surgery, with a centrally located, noncircular first conduit having two generally planar, longitudinally extending wall surfaces joined at about a 90 degree angle, with those two walls joined by a third curved wall as measured in cross-section. The outer wall thickness is substantially constant.

U.S Pat. No. 4,753,640, to Nichols, et al., for "Catheters and Methods", discloses in FIGS. 1–9, a catheter assembly with one or more lumens having D-shaped axial lumens with linear wall surfaces joined tangentially. At least one longitudinally extending wall surface is curved when measured in cross-section.

U.S Pat. No. 4,947,852, to Nassi, et al., for "Apparatus and Method for Continuously Measuring Volumetric Blood Flow using Multiple Transducer and Catheter for use Therewith", discloses in FIG. 2, a noncentrally located guidewire lumen with an even number of walls of constant thickness.

U.S Pat. No. 5,271,410, to Wolzinger, et al., for "Catheter with Rapid Response Thermistor and Method", discloses in FIG. 2, four noncircular, noncentrally located lumens. At least one longitudinally extending wall surface is curved when measured in cross-section. The outer wall thickness is substantially constant.

Commonly owned copending application Ser. No. 07/944,756, to Molacek, et al for a Medical Electrical Lead discloses in FIG. 2, a multilumen lead with generally rounded-corner triangular or "pie-shaped", noncentrally located lumens in cross-section. The outer wall thickness is substantially constant as the minimum wall thickness for adequate electrical isolation between the lumens imposes a design constraint on such leads. Increases in diameter of a circular lumen result in increases in achievable minimum lead diameter.

Single lumen catheters are typically circular in shape and have a constant wall thickness thereby maximizing the lumen inner diameter while minimizing the lumen outer diameter. This permits the largest guidewire to fit in the catheter with the smallest outer diameter. Multilumen catheters are often pie shaped and have a constant wall thickness as this tends to permit the greatest number of lumens in the smallest area. Catheter walls collapse when submitted to high levels of stress. Friction results when the guidewire comes in contact with the lumen walls. The object of the invention is to create a lumen with a wall configuration which will tolerate higher levels of stress yet result in minimum friction between the guidewire and inner lumen.

SUMMARY OF THE INVENTION

The features and advantages of the present invention, as well as others, are accomplished by providing a catheter body with a single centrally located guidewire lumen having an odd number of longitudinally extending, generally planar, inner wall surfaces. Each wall surface has a radius of curvature in excess of the guidewire's radius of curvature, as measured in cross section. The wall surfaces are joined to one another by longitudinally extending corner surfaces, each corner surface having a radius of curvature less than the guidewire's radius of curvature, as measured in cross section. The wall surfaces and corner surfaces are formed of alternating thicknesses to the outer diameter. An odd number of wall surfaces are preferred, as for example, 5, 7 or 9 wall surfaces. The lumen is sized to receive a removable guidewire.

Computer modeling revealed that an odd number of generally planar, longitudinally extending wall surfaces of a centrally located lumen when viewed in cross-section tolerated more stress than did a circular lumen with uniform wall thickness. The alternating areas of thickness in lumens with an odd number of longitudinally extending, generally planar walls, increased the level of stress which could be tolerated. Such alternating areas of thickness also results in less points of contact with the guidewire thereby reducing friction. An odd number of walls were also observed to be more resistant to kinking and collapsing than were even numbers of walls.

DETAILED DESCRIPTION OF THE PREFERRED EMBODIMENTS

Figure 1:
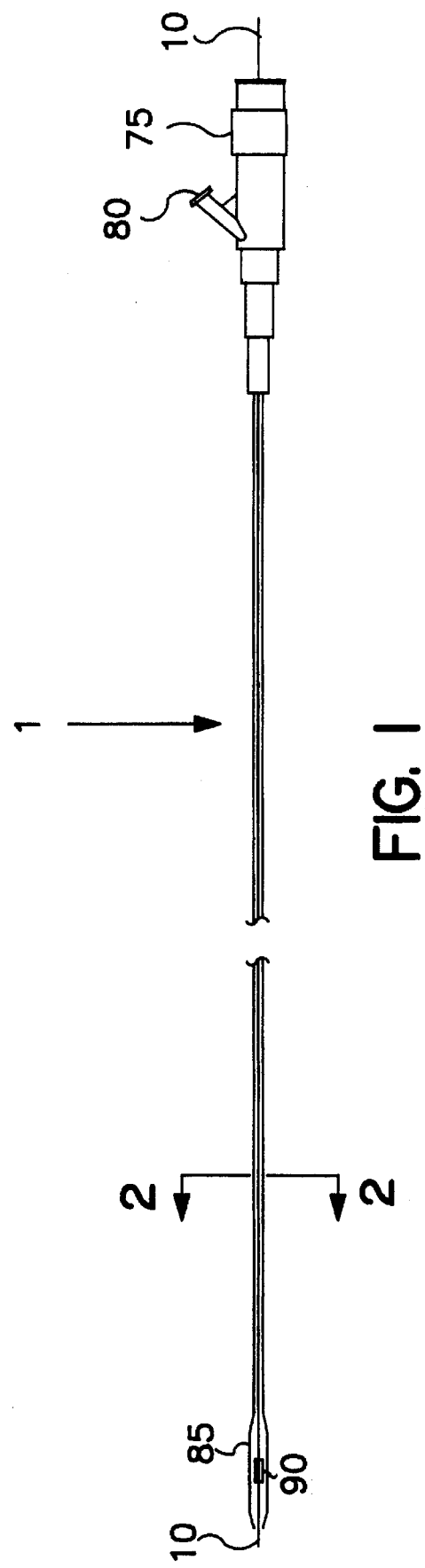
FIG. 1 is a diagram of a catheter which incorporates a preferred embodiment of the present invention.

FIG. 1 is a diagram of a catheter 1, which incorporates the preferred embodiment of the invention. Typical catheter components include a manifold 75, a port for various purposes, as for example, an inflation port 80, a marker band 90 for fluoroscopy, and if the catheter is used for angioplasty, a balloon 85. It is understood by those skilled in the art that lumens of the shape disclosed could be used in catheter applications other than angioplasty.

In over-the-wire systems, the guidewire 10 is threaded through the vascular system to the site of the stenosis and the catheter 1 subsequently tracked over it to the stenosis. The catheter 1 is withdrawn over the guidewire 10 and another catheter can be slid into place over it if a different size or type of catheter is required.

Figure 2:
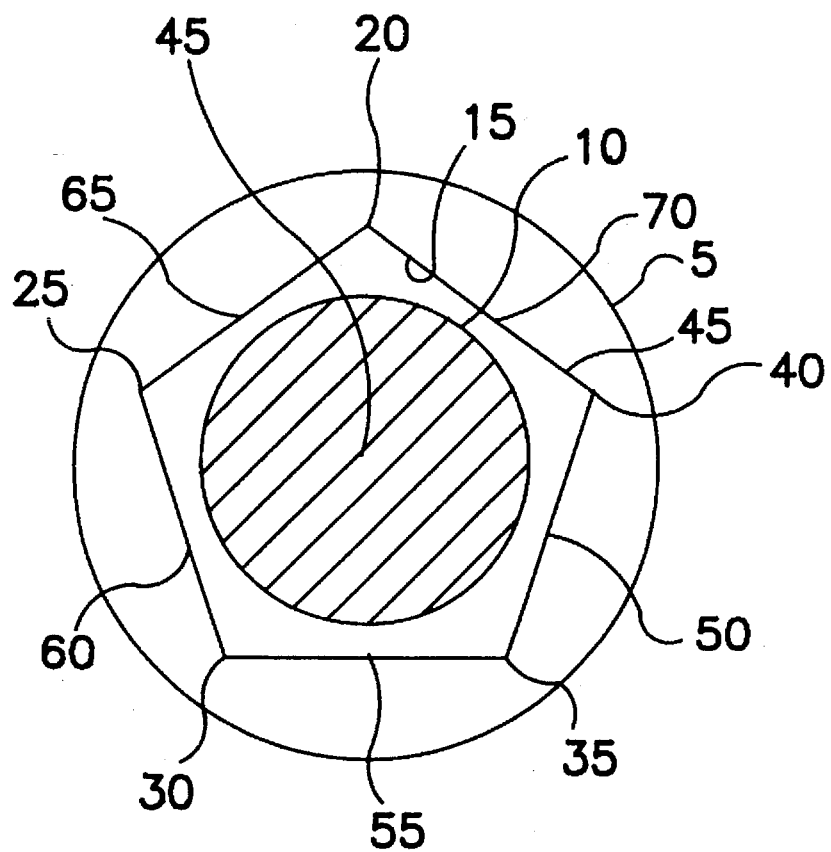
FIG. 2 is a cross-sectional view of the catheter of FIG. 1.

FIG. 2 is a cross-section through the catheter 1 body. In this view, it can be seen that the catheter 1 is provided with a five sided polygon shaped guidewire lumen 15. Other odd numbers of sides could also be used, such as 7 sides or 9 sides. With a polygon shaped guidewire lumen 15, contact will be limited to discrete points of contact along walls 50, 55, 60, 65 and 70, and not in corners 20, 25, 30, 35 and 40. The thickness between the outer diameter 5 and the inner diameter is greater along the walls 50, 55, 60, 65 and 70 than in the corners 20, 25, 30, 35 and 40. Because of the areas of greater thickness, the catheter is more resistant to collapse than is a conventional lumen with uniform wall diameter.

The guidewire lumen 15 is an extruded tubing made of conventional catheter materials, such as nylon or High/Lo Density Polyethylene (HDPE or LDPE). The guidewire can be made of conventional guidewire materials, such as stainless steel. The outside diameter 5 of the tubing has a circular cross section. When a polygon shaped guidewire lumen 15 is used, suitable configuration and dimensions include the following. Wall surface 70 joins wall surface 50 tangentially at corner 40. Wall surface 50 joins wall surface 55 tangentially at corner 35. Wall surface 55 joins wall surface 60 tangentially at corner 30. Wall surface 60 joins wall surface 65 tangentially at corner 25. Wall surface 65 joins wall surface 45 tangentially at corner 20.

In a catheter 1 with a radius of 0.0105 inches and an outside diameter of 0.021 inches, each wall 50, 55, 60, 65 and 70 could be 0.0106 inches long, with a distance of 0.009 inches from the center of the guidewire lumen 45 to any corner 20, 25, 30, 35 or 40. The distance from the center of any wall surface 50, 55, 60, 65, or 70 to the center of the guidewire lumen 45 is 0.0073 inches.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 1 | Catheter Body |
| 5 | Catheter Outer Diameter |
| 10 | Guidewire |
| 15 | Guidewire Lumen |
| 20 | Corner |
| 25 | Corner |
| 30 | Corner |
| 35 | Corner |
| 40 | Corner |
| 45 | Guidewire Lumen Center |
| 50 | Wall |
| 55 | Wall |
| 60 | Wall |
| 65 | Wall |
| 70 | Wall |
| 75 | Manifold |
| 80 | Inflation Port |
| 85 | Balloon |
| 90 | Marker Band |

What is claimed is:

1. A medical catheter comprising:

an elongated catheter body having a single centrally located lumen extending longitudinally along the catheter body;

a removable guidewire extending through the lumen, the guidewire having a first radius of curvature, as measured in cross section through said catheter body, the guidewire being sized to slidingly fit within the centrally located lumen; and wherein said lumen has an odd number of longitudinally extending, generally straight, inner wall surfaces, the inner walls being joined to one another by longitudinally extending corner surfaces, the inner walls and the corner surfaces being formed by alternating thicknesses to an outer diameter, the corner surfaces' thickness to the outer diameter being less than the inner walls' thickness to the outer diameter.

2. A catheter according to claim one wherein the inner wall surfaces are generally planar.

3. A catheter according to claim one wherein the lumen has a first, second, third, forth and fifth longitudinally extending inner wall surface;

the first wall joined to the second wall by a longitudinally extending first corner surface;

the second wall joined to the third wall by a longitudinally extending second corner surface;

the third wall joined to the forth wall by a longitudinally extending third corner surface;

the forth wall joined to the fifth wall by a longitudinally extending forth corner surface; and the fifth wall joined to the first wall by a longitudinally extending fifth corner surface.

4. A catheter according to claim three, wherein the first, second, third, forth and fifth wall surfaces are 0.0106 inches in length.

5. A catheter according to claim three wherein the first, second, third, forth and fifth corners are 0.009 inches in length from the center of the lumen.

6. A catheter according to claim three having a length of 0.0073 inches from the center of the first, second, third, forth and fifth wall surfaces to the center of the catheter.

7. A catheter according to claim three having a length of 0.0105 inches from the outer diameter to the center of the catheter and an outside diameter of 0.0105 inches.

8. A catheter according to claim one, wherein the lumen has seven longitudinally extending inner wall surfaces, joined to one another by longitudinally extending corner surfaces.

9. A catheter according to claim one, wherein the lumen has nine longitudinally extending inner wall surfaces, joined to one another by longitudinally extending corner surfaces.

10. A medical catheter comprising:

an elongated catheter body having a single centrally located lumen extending longitudinally along the catheter body, the catheter body having an outer diameter;

a removable guidewire extending through the lumen, the guidewire having a first radius of curvature, as measured in cross section through said catheter body, the guidewire being sized to slidingly fit within the centrally located lumen; and wherein said lumen has an odd number of longitudinally extending, generally straight, inner wall surfaces, the inner walls being joined to one another by longitudinally extending corner surfaces, the inner walls and the corner surfaces being formed by alternating thicknesses of the inner wall surfaces and the corner surfaces to the catheter body outer diameter, the corner surfaces' thickness to the outer diameter being less than the inner walls' thickness to the outer diameter.

11. A catheter according to claim ten wherein the inner wall surfaces are generally planar.

12. A catheter according to claim ten wherein the lumen has a first, second, third, forth and fifth longitudinally extending inner wall surface;

the first wall joined to the second wall by a longitudinally extending first corner surface;

the second wall joined to the third wall by a longitudinally extending second corner surface;

the third wall joined to the forth wall by a longitudinally extending third corner surface;

the forth wall joined to the fifth wall by a longitudinally extending forth corner surface;

the fifth wall joined to the first wall by a longitudinally extending fifth corner surface.

13. A catheter according to claim twelve, wherein the first, second, third, forth and fifth wall surfaces are 0.0106 inches in length.

14. A catheter according to claim twelve wherein the first, second, third, forth and fifth corners are 0.009 inches in length from the center of the lumen.

15. A catheter according to claim twelve having a length of 0.0073 inches from the center of the first, second, third, forth and fifth wall surfaces to the center of the catheter.

16. A catheter according to claim twelve having a length of 0.0105 inches from the outer diameter to the center of the catheter and an outside diameter of 0.0105 inches.

17. A catheter according to claim ten, wherein the lumen has seven longitudinally extending inner wall surfaces, joined to one another by longitudinally extending corner surfaces.

18. A catheter according to claim ten, wherein the lumen has nine longitudinally extending inner wall surfaces, joined to one another by longitudinally extending corner surfaces.

19. A medical catheter comprising:

an elongated catheter body having a single centrally located lumen extending longitudinally along the catheter body, the catheter body having an outer diameter;

a removable guidewire extending through the lumen, the guidewire having a first radius of curvature, as measured in cross section through said catheter body, the guidewire being sized to slidingly fit within the centrally located lumen; and wherein said lumen has an odd number of longitudinally extending, generally straight, inner wall surfaces, the inner walls being joined to one another by longitudinally extending corner surfaces, the inner walls and the corner surfaces being formed by alternating thicknesses of the inner wall surfaces and the corner surfaces to the catheter body outer diameter, at least one corner surface thickness to the outer diameter being less than at least one inner wall thickness to the outer diameter.

* * * * *